United States Patent [19]

McClelland et al.

[11] Patent Number: 5,120,548
[45] Date of Patent: Jun. 9, 1992

[54] SWELLING MODULATED POLYMERIC DRUG DELIVERY DEVICE

[75] Inventors: Gregory A. McClelland; Gaylen M. Zentner, both of Lawrence, Kans.

[73] Assignee: Merck & Co., Inc., Rahway, N.J.

[21] Appl. No.: 433,056

[22] Filed: Nov. 7, 1989

[51] Int. Cl.$^5$ .......................... A61K 9/24; A61K 2/00; A61K 31/74
[52] U.S. Cl. ...................................... 424/473; 424/424
[58] Field of Search .................... 424/78, 81, 424, 427, 424/435, 437, 449, 473

[56] References Cited

U.S. PATENT DOCUMENTS

| 4,309,996 | 1/1982 | Theeuwes | 128/260 |
| 4,350,271 | 9/1982 | Eckenhoff | 224/386.5 |
| 4,642,233 | 2/1987 | Urquhart et al. | 424/19 |
| 4,723,957 | 2/1988 | Magruder et al. | 424/78 |
| 4,747,847 | 5/1988 | Magruder et al. | 604/892.1 |
| 4,755,180 | 7/1988 | Ayer et al. | 604/892.1 |
| 4,839,177 | 6/1989 | Columbo et al. | 424/482 |

Primary Examiner—Thurman K. Page
Assistant Examiner—G. S. Kishore
Attorney, Agent, or Firm—Donald J. Perrella; Melvin Winokur; Joseph F. DiPrima

[57] ABSTRACT

A controlled release drug delivery device, comprised of swellable polymers, whose degree of swelling in an environment of use is controlled by swelling modulators blended within the polymers, is disclosed. The swelling modulators can include buffers, osmagents, surfactants or combinations thereof surrounded by a microporous coating or interspersed within individual matrices. The combination of controlled release swelling modulators with swellable polymers may be applied to regulate patterns of beneficial agent (typically a drug) release.

6 Claims, 5 Drawing Sheets

SWELLING MODULATED POLYMERIC DRUG DELIVERY DEVICE

BACKGROUND OF THE INVENTION

Swellable polymeric controlled release drug delivery devices often suffer from the disadvantage that unexpected or variant conditions in the environment of use, for example levels of acidity, can predominate the rate or pattern with which the device releases its drug or active agent. For example, the rate of swelling (and hence drug release) of a pH sensitive, swellable, polymeric drug delivery device introduced into the gastrointestinal tract will vary depending on the acidity of the particular part of the tract through which the device passes. Such variation defeats the desired objective of drug release that is controlled by the dosage form rather than the environment and can, in fact, be detrimental to the patient. Overdosing or underdosing could occur if, at any one site (or within any given patient), conditions are such that an unwanted degree of polymeric swelling or deswelling causes substantially more or less of the drug to be released.

Although swellable, polymeric drug delivery devices are well known and are described, e.g., in U.S. Pat. Nos. 4,839,177; 4,747,847; 4,723,957; 4,350,271; 4,309,996; and 4,642,233; known polymeric devices fail to solve the aforementioned problems attendant to the use of polymeric drug delivery devices in environments of use whose conditions vary from location to location. Additionally, provision for control of polymer swelling and attendant beneficial agent release in variable or non-variant environments have not been disclosed previously.

SUMMARY OF THE INVENTION

We have discovered that, by incorporating controlled release swelling modulators, such as buffers, osmagents, surfactants or combinations thereof surrounded by a microporus coating or interspersed within individual matrices, into swellable polymer drug delivery devices, the degree of polymer swelling can be regulated for a prolonged period to achieve either desired constant or intermittent drug delivery. Buffers, osmagents, surfactants or combinations thereof, per se, which serve as swelling modulators and which are referred to hereinafter as rapid release elements can also be added.

U.S. Pat. No. 4,755,180 to Ayer (Ayer '180) describes solubility modulation of active agent but not of swellable polymers, by using buffers and osmagents. Applicants copending U.S. patent application Ser. Nos. 348,099 and 384,116, disclosed claim solubility modulation of active agent using surfactants and complexing agents, but do not suggest modulation of polymer swelling using those agents.

The effects of buffer and surfactant swelling modulators in typically aqueous fluids may be related to specific influences on the ionization state of the polymer and degree of wetting of the polymer by the fluid of the environment, respectively. Osmagents influence swelling through specific effects such as common ion effects or through non-specific effects on the thermodynamic activity of water or through electrostatic shielding effects. The ability of the polymer chains to separate and to compete for and attract available water is thereby modified and swelling is affected. For example, a swellable polymer such as poly(acrylic acid) containing acidic functional groups swells to a greater extent in the presence of an alkaline swelling modulator (buffer) due to increased ionization of the acid groups. The now ionized groups can electrostatically repel one another as well as interact more strongly with water, both effects resulting in an expansion of volume (swelling). In the presence of the osmagent sodium chloride, the swelling of the sodium salt of poly(acrylic acid) is suppressed. However, other swellable polymers that are admixed with osmagents may exhibit increased swelling due to osmotic inhibition of water in response to the osmotic pressure of the osmagent. Surfactants, which lower the interfacial tension between the swellable polymers and the aqueous environment, would enhance polymer/water interactions (work of adhesion increased) and alter the observed swelling behavior.

The swelling modulators are formulated into a controlled release form by either coating the modulator with a microporous wall or by incorporating the modulator into individual matrices. These coated or matrix-enclosed swelling modulators are then blended with a swellable polymer (usually a water-swellable polymer) in an amount that will regulate polymer swelling for a prolonged period to a degree that achieves the desired release profile of the beneficial agent. Rapid release swelling modulator may optionally be included to modulate swelling during the start-up phase of beneficial agent release.

The combination of swelling modulators, swellable polymer and beneficial agent can be configured into various core geometries (usually tablets, pellets or particulates) and can be either: (1) coated with an insoluble wall containing at least one exit means (i.e., hole) for release of the beneficial agent; (2) coated with an insoluble wall containing leachable additives which form pores in the environment of use, thereby allowing passage of beneficial agent through the wall; or (3) uncoated.

In the coated configurations, a uniform mixture comprised of beneficial agent, swellable polymer, controlled and rapid release swelling modulator and other excipients can form the core composition. With both types of coating in the environment of use the beneficial agent is expelled through either the release means (i.e., hole) or the pores in the coating. In cases where the holes(s) or pores in the coat are of sufficient size, the swellable polymer and controlled release swelling modulator may also be expelled into the environment. Another coated variation includes bilayered cores comprised of a first layer comprised of beneficial agent and excipients, and a second layer comprised of a mixture of swelling polymer, controlled and rapid release swelling modulator, and other formulation excipients. In this configuration the beneficial agent is substantially released through either holes(s) or pores in the coat without concomitant release of swellable polymer or controlled release swelling modulator. Laminates of semipermeable and microporous coats also fall within the scope of the disclosure. The microporous wall may either directly contact the semipermeable wall to form a bilaminate, or the microporous wall may be separated from the semipermeable wall by a layer of fluid soluble material, which may optionally contain drug, which dissolves in the environment of use, creating a fluid layer separating the microporous and semipermeable walls.

In operation, fluid from the environment of use contacts the controlled release swelling modulators, releasing the swelling modulating agent(s) in a controlled fashion into the immediate environment of the swelling polymer. The rate and extent of polymer swelling, and hence rate of drug delivery, is thereby controlled. The swelling polymer can act as either: (1) a driving force against a composition containing a beneficial agent in a coated device formulation whereby the beneficial agent is expelled through hole(s) or pore(s) in the coat; or (2) a swellable matrix which, upon swelling increases in permeability to a beneficial agent which may then more freely diffuse or flow out to an environment of use. In all cases the desired beneficial agent release profile is a function of the degree of polymer swelling which in turn is modulated by the controlled release swelling modulator; both continuous or intermittent-bolus beneficial agent release can be achieved at predetermined times or sites.

Swelling modulator agents include buffers, osmagents, surfactants, and combinations thereof. Buffers are comprised of acids and bases that can influence pH such as adipic and citric acid, sodium and potassium phosphates, magnesium oxide and the like. Osmagents are comprised of water soluble salts which influence ionic strength, such as sodium chloride, potassium carbonate, calcium chloride, sodium acetate and other organic and inorganic salts.

Surfactants are comprised of those compounds that decrease surface and interfacial tension and serve to enhance and facilitate wetting. As such they serve to promote interactions between water and swellable polymers and hence modulate the swelling properties of those polymers. Generally, the surfactants are amphipathic molecules comprised of a hydrophobic part and a hydrophilic part. The surfactants useful in the present invention can be anionic, cationic, nonionic or amphoteric. The anionic surfactants include sulfated, sulfonated, or carboxylated esters, amide, alcohols, ethers, aromatic hydrocarbons, aliphatic hydrocarbons, acylated amino acids and peptides. Metal alkyl phosphates are another class of anionic surfactant. Typically, cationic surfactants are primary, secondary, tertiary or quarternary alkylammonium salts, acylated polyamines, and salts of heterocyclic amines. Nonionic surfactants are typically esters and ethers of polyoxyalkylene glycols, polyhydric alcohols, or phenols. Poloxamers and poloxamines are included as nonionic surfactants. Surfactants are discussed in *Surfactant Systems, Their Chemistry, Pharmacy, and Biology*, D. Attwood and A. T. Florence, Chapman and Hall Pub. Co., 1983.

BREIF DESCRIPTION OF THE DRAWINGS

DETAILED DESCRIPTION OF A PREFERRED EMBODIMENT

Figure 1:
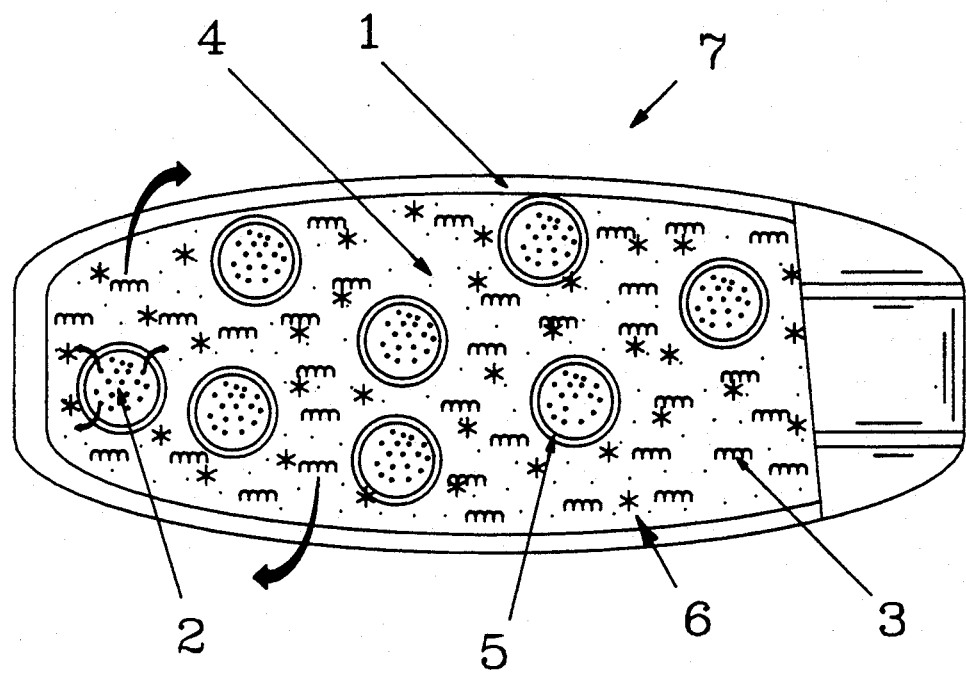
FIG. 1 illustrates a polymeric drug delivery device manufactured in accordance with the present invention.
Figure 2:
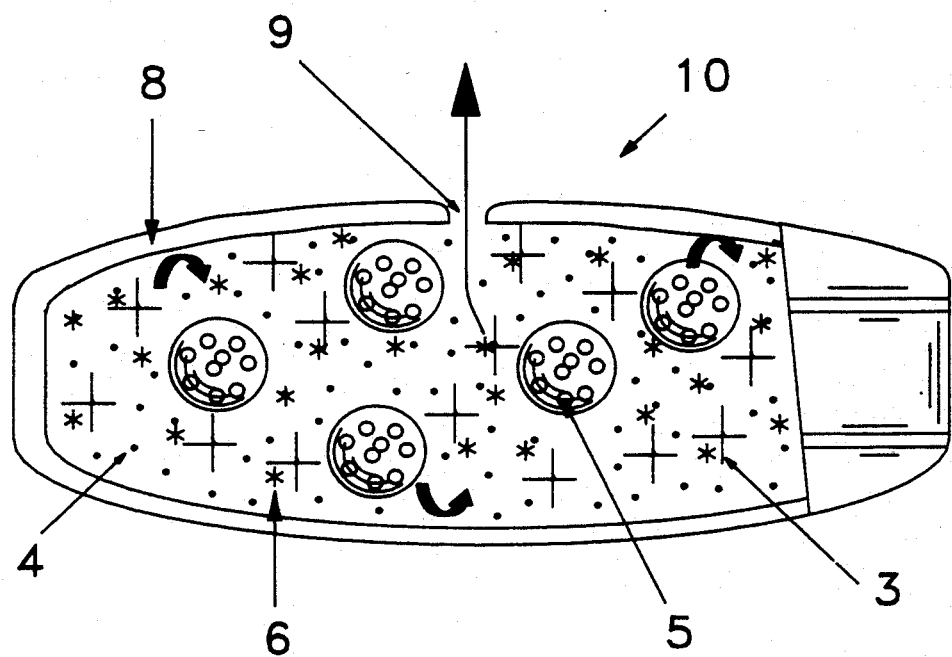
FIG. 2 illustrates an embodiment of the present invention in which the device is surrounded by a water-insoluble, semipermeable wall.
Figure 3:
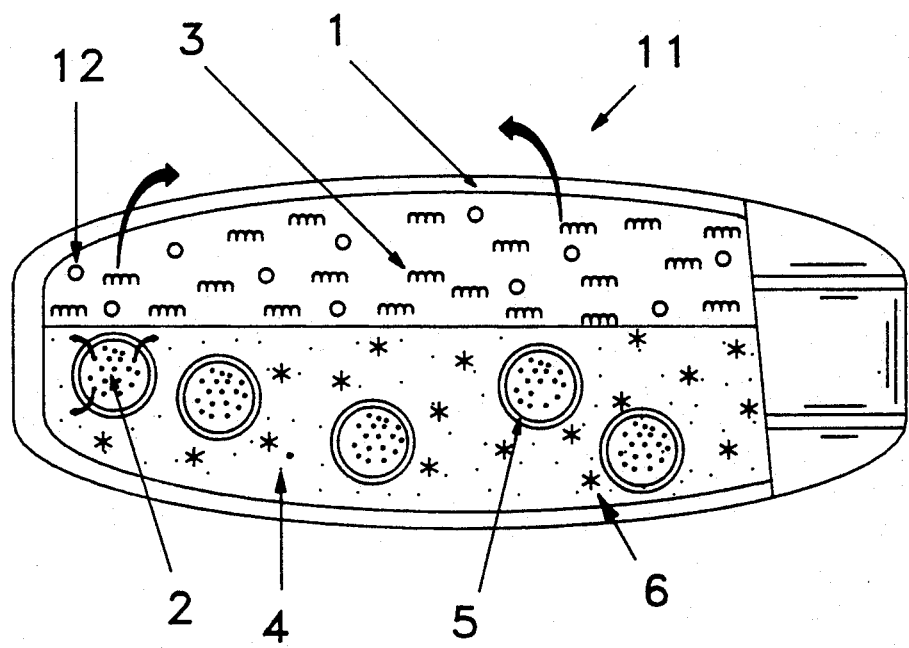
FIG. 3 illustrates a bilayered tablet version of the invention.
Figure 4:
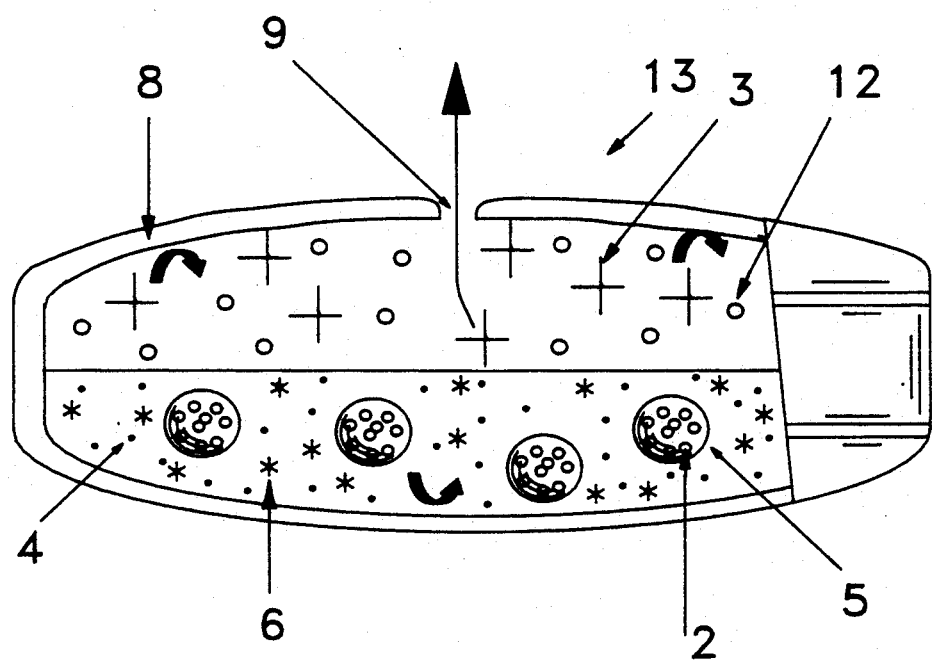
FIG. 4 illustrates still another bilayered tablet embodiment of the invention.
Figure 5:
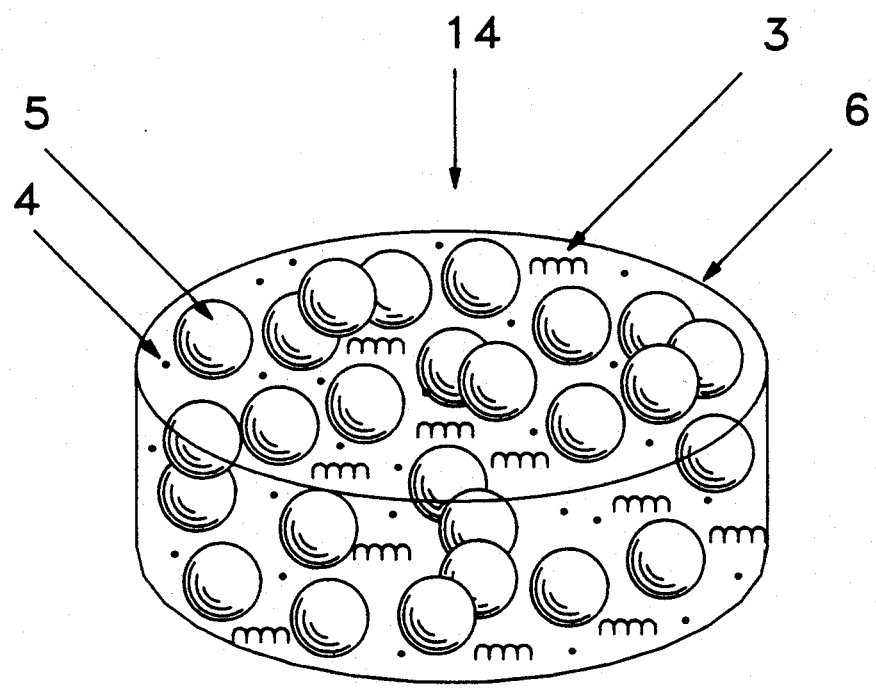
FIG. 5 illustrates an embodiment of the invention in which the device is a monolithic swellable polymer matrix.

FIG. 1 is a schematic representation of one embodiment of the instant invention. The device, 7, has a core composition comprised of drug, 3, swellable polymer, 6, and swelling modulator, 2, contained in a controlled release unit, 5, which becomes the controlled release swelling modulator. Rapid release swelling modulator, 4, may be dispersed among other excipients as needed to form the composite core tablet suitable for the application of a microporous, water-insoluble wall, 1. In operation water permeates wall, 1, entering the core compartment where water soluble drug, 3, rapid release swelling modulator 4, and excipients dissolve. The swellable polymer, 6, swells to a degree as modulated by the rapid release swelling modulator, 4. The water then permeates the controlled release swelling modulator units, 5, and the swelling modulator(s), 2, are released from 5 at a controlled rate into the core environment where the swelling of polymer, 6, is modulated for a prolonged period. Swelling modulator, 4, is included to modulate the swelling of the polymer during the start-up of swelling modulator release from element 5. The pressure created by the swelling polymer, which is proportional to the degree of swelling, serves to eject drug laden solution out of the core, across the wall and into the environment. FIG. 2 is another embodiment of the instant invention. The device, 10, is surrounded by a water-insoluble semipermeable wall, 8, containing an aperture(s), 9, for the release of core compartment components. All other elements are as defined previously. In operation, water is imbibed into the core through the semipermeable wall, 8. The water further enters the controlled release swelling modulator unit, 5, to release swelling modulator at a defined rate. The swelling of the polymer, 5, is thereby controlled. Contents of the device are expelled through the aperture(s), 9, in a pattern that reflects the degree of polymer swelling. FIG. 3 represents another embodiment of the present invention. The device, 11, is a bilayered tablet containing several elements described previously. The device also contains excipients, 12, which may be necessary to form a tablet suitable for the application of a microporous, water-insoluble wall, 1. FIG. 4 is another schematic representation of an embodiment of the instant invention. The device, 13, is a bilayered tablet configuration comprised of elements described previously. FIG. 5 is another embodiment of the instant invention where device, 14, is a monolithic swellable polymer matrix, 6, throughout which are dispersed elements defined previously.

In one embodiment of the present invention, a plurality of controlled release swelling modulators are prepared by coating one or more types of the aforementioned swelling modulators with water insoluble, water permeable, polymeric materials using spray coating techniques with water insoluble, water permeable, polymeric materials. Examples of appropriate polymers for coating applications include cellulose esters and ethers such as cellulose acetates, cellulose butyrates, cellulose propionates, ethylcellulose, and mixed cellulose esters, acylated polysaccharides, polyurethanes, polyacrylate and polymethacrylate polymers and derivatives. Preferred coating thicknesses range from about 1 to about 1,000 microns, most preferably between about 20 to 500 microns. Plasticizers, including, but not limited to, phthalates (such as dialkyl phthalates), alkyl and aryl phosphates, or glycol ethers and esters, can be added, in a range of from about 0.01 to 500 parts per 100 parts wall material, to the coating materials to impart flexibility. In this embodiment, the polymer coat contains at least one pore forming additive. The pore forming additive is any material that can be leached from the insoluble polymer material upon exposure to the environment of use, thereby forming a microporous coating possessing from about 5% to about 95% pores of a size ranging from about 10 angstroms to about 100 microns.

Alternatively, the controlled release swelling modulators may be made in a matrix form by combining the modulator with matrix forming materials by techniques such as wet granulation, fluid bed granulation, casting, direct compression, and spheronization (e.g. marumerization). Appropriate matrix materials are semisolid to solid and dissolve or erode in the fluid which permeates the core from the environment of use, or are insoluble materials that serve as diffusion media to modulate the leaching of the swelling modulator. Materials suitable as matrix materials include those described previously for use as coating materials and additionally waxes, polymeric glycols, gums, rubbers, water soluble cellulose derivatives such as hydroxypropylmethyl cellulose, water soluble polyacrylate and polymethacrylate derivatives, and the like.

These coated or matrix enclosed controlled release swelling modulators are then blended or mixed with water insoluble, water-swellable polymers such as the hydrogels described in "Hydrogels in Controlled Drug Delivery", N. B. Graham, NATO ASI Series E. Col. Vol. 106, pages 170-194 (1986) and in "Hydrogels in Medicine and Pharmacy", Vols. I, II, III, N. A. Pepas, Ed., CRC Press, (1987), and in U.S. Pat. Nos. 3,640,741; 3,865,108; 3,992,562; 4,002,173; 4,014,335; and 4,207,893; and in "Handbook of Common Polymers", Scott and Roff, published by the Chemical Rubber Company.

The presently preferred swellable polymer materials are hydrogels that swell in, and retain a significant amount of, water. Polymeric hydrogels (which can be crosslinked or uncrosslinked) swell or expand significantly in water, usually exhibiting a 2 to 50 fold or greater volume increase. The cross-linked polymers will swell and will not dissolve; uncrosslinked polymers may dissolve subsequent to swelling although dissolution is not a necessary consequence. Examples of swellable polymers include: crosslinked polymethacrylate and polyacrylate polymers derivatized with hydroxyalkyl and/or ionizable acidic/basic functional groups, and their respective salt forms; crosslinked polyvinyl-pyrrolidone; crosslinked polyvinyl alcohols; poly(ethylene oxide)s; polymethacrylamides and polyacrylamides; derivatized or modified cellulosic polymers such as crosslinked sodium carboxymethylcellulose, crosslinked hydroxypropylcellulose, starch graft copolymers, crosslinked hydroxypropylmethylcellulose, crosslinked dextrans and agarose, and microcrystalline cellulose; carboxymethylamide; and polyelectrolytes.

Beneficial agents, including inorganic and organic compounds useful in the present invention includes substances that produce localized or systemic effects in humans or animals resulting in desirable functions and responses. Examples include but are not limited to amitripytline, haloperidol, diazepam, cyclobenzaprine, carbidopa, levodopa, acetaminophen, isoproterenol, chlorpheniramine, digoxin, timolol, nifedipine, diltiazem, methyldopa, enalapril, lysinopril, felodipine, hydrochlorothiazide, simvastatin, lovastatin, ethinyl estradiol, dexamethasone, indomethacin, sulindac, diflunisal, ranitidine, famotidine, omeprazole, norfloxacin, ivermectin, pravistatin. Typical beneficial agent loadings range from about 0.05 nanograms to 5 grams or more.

In coated embodiments of the invention a core compartment containing various admixtures of swelling polymer, controlled release swelling modulator(s) and beneficial agent can be coated with a wall containing at least one exit for the delivery of drug. If the wall is of a microporous nature it can be comprised of materials and methods as described previously for the wall surrounding the controlled release swelling modulator. Alternatively, the wall may be a semipermeable wall which is permeable to the passage of fluid but impermeable to the passage of solutes. A release means for the delivery of drug is then made in the semipermeable wall by those means and methods suitable for releasing the drug.

Examples of appropriate polymers for coating applications include cellulose esters and ethers such as cellulose acetates, cellulose butyrates, cellulose propionates, ethylcellulose, and mixed cellulose esters, acylated polysaccharides, polyurethanes, polyacrylate and polymethacrylate polymers and derivatives.

Additional, preferred specifications for both the microporous and semipermeable wall configurations include:

1. Plasticizers and Flux Regulating Additives: 0 to 50, preferable 0.001 to 50, parts per 100 parts wall material.
2. Surfactant additives: 0 to 40, preferable 0.001 to 40, parts per 100 parts wall material.
3. Wall Thickness: 1 to 1,000, preferable 20 to 500, microns typically, although thinner and thicker fall within the invention.

The expression "release means" or hole(s) as used herein are comprised of those means and methods suitable for releasing the drug from the core through the semipermeable wall. The expression includes the following: an aperture, orifice, bore, hole, or porous element through which product can migrate, hollow fibers suitable for passing the drug, capillary tubes, cracks, and the like. The expression also includes bioerodible materials that erode in the environment of use to produce passageways of precontrolled dimensions. Typical bioerodible materials suitable for forming a passageway include erodible poly(glycolic) acid and poly(lactic) acid fibers, poly(ortho ester)s, erodible gelatinous filaments, poly(vinyl alcohol), and the like.

Water insoluble, permeable, non-rate controlling microporous walls may be applied to core composition masses prior to the application of the semipermeable wall or subsequent thereto by spray coating procedures. The microporous wall may either directly contact the semipermeable wall to form a bilaminate structure, or the microporous wall may be separated from the semipermeable wall by a layer of fluid soluble material, which may optionally contain drug, which dissolves in the environment of use, creating a fluid layer separating the microporous and semipermeable walls.

In embodiments where the rate controlling wall surrounding the core is microporous in nature the coat is comprised of polymers discussed previously and contain water soluble, leachable, additives. The additives suitable for the present application are those water soluble compounds of organic or inorganic origin and are illustrated by alkali metal and earth salts such as sodium chloride and calcium chloride, saccharides and polyols such as sorbitol, sucrose, mannitol and poly(alkylene glycols), and other water soluble organics such as nicotinamide and tromethamine. The pore forming additives are typically present at 0.1 to 90% of the combined weight of polymer and pore forming additive.

The invention is further illustrated by the following examples.

EXAMPLES

In Examples 1, 2 and 3, a controlled release sodium chloride (C.R. NaCl) source is prepared as a controlled release swelling modulator (C.R.S.M.) to regulate (i.e., suppress) the swelling of a sodium polyacrylate hydrogel polymer (Aqua Keep TM J-550; Seitetsu Kagaku, Co. Ltd.) to optimize the release profiles from osmotic controlled release beneficial agent (C.R.B.A.) delivery devices. The C.R. NaCl is prepared from 700 g aliquots of sodium chloride crystals passing a #20 and retained on a #30 sieve (600 micron opening) then coated with a microporous wall in standard fluidized-bed spray coating equipment (Uni-Glatt). The spray solution is 100 g cellulose acetate butyrate 381-20 dissolved in a 3:1 dichloromethane/methanol solvent blend. About 20 g sorbitol dissolved in a water/methanol solvent blend is then added as a pore forming agent to influence the release of NaCl. The sodium chloride crystals are coated to release sodium chloride continuously over various periods of time, with longer release times corresponding to thicker coats.

EXAMPLE 1

Diltiazem hydochloride is a highly water soluble drug (having a solubility of greater than 500 mg/ml at 37° C.). Release of this drug from osmotic pump C.R.B.A. delivery devices is about 50% zero-order (in which a saturated solution of drug is expelled) followed by a continually decreasing first-order release rate (during which a subsaturated solution of drug is expelled). By allowing sodium chloride to meter into a hydrogel polymer compartment over a several hour period through incorporation of C.R. NaCl elements, swelling of the hydrogel may be suppressed. Once the sodium chloride in the C.R. NaCl elements is exhausted, which may be timed to correspond to the onset of the first-order rate of diltiazem hydrochloride release, the polymer hydrates substantially and expels the remaining subsaturated diltiazem hydrochloride from the drug compartment at an increased rate to effect a near zero-order release of greater than 70% of the diltiazem hydrochloride.

Such C.R.B.A. devices are manufactured according to the following procedures. A bilayer osmotic device for the controlled and continuous release of the beneficial agent diltiazem hydrochloride is made as follows: 360 mg diltiazem hydrochloride is mixed with 85 mg adipic acid, 70 mg citric acid, and 5% w/w polyvinylpyrrolidone 29-32K and compressed in a Manesty tableting press fitted with a 7.1 mm×17.4 mm caplet punch to produce a layer of drug composition. Next 100 mg of Aqua Keep TM J-550 is mixed with 50 mg C.R. NaCl (coated to give 6-7 hours continuous sodium chloride release) and 20 mg rapid release sodium chloride. This mixture is added to the Manesty press and compressed to form a layer of swelling modulated hydrogel in contact with the drug compartment. The resulting bilayered cores are then coated with a semipermeable wall. 72 g of cellulose acetate having an acetyl content of 39.8% is dissolved in 600 ml methanol and 980 ml methylene chloride, then sprayed onto the bilayered cores in a fluidized bed machine until a 150 micron thick coat is achieved. The coated devices are dried for 72 hours at 50° C. and a 0.015 inch diameter hole drilled through the semipermeable wall on the drug side of the bilayer core connecting the drug containing layer with the exterior of the devices.

EXAMPLE 2

The procedures of Example 1 are repeated to form bilayered core tablets. A microporous coat is then applied to these cores as follows:

72 g cellulose acetate having an acetyl content of 39.8% is dissolved in a dichloromethane/methanol solvent blend. To this is added 54 g sorbitol as a pore-former dissolved in a water/methanol solvent blend. This solution is sprayed onto the cores in a commercial Uni-Glatt fluidized bed coating machine. A wall 400 microns thick is applied to the tablet cores.

EXAMPLE 3

An osmotic therapeutic device for the controlled and continuous oral release of diltiazem hydrochloride is made as follows: 360 mg diltiazem hydrochloride is mixed with 85 mg adipic acid, 70 mg citric acid, 100 mg Aqua Keep TM J-550 and 50 mg C.R. NaCl (coated to give 6-7 hours continuous sodium chloride release). This mixture is granulated with 5% w/w polyvinylpyrrolidone 29-32K dissolved in ethanol. The resultant granules are a homogeneous mixture and are tableted to form a monolithic core compartment in a Manesty tableting press fitted with a 7.1 mm×17.4 mm caplet punch. This core compartment is then coated with either a semipermeable coat with an orifice drilled through the semipermeable coat as described in Example 1 or coated with a microporous coat as described in Example 2.

EXAMPLE 4

In accordance with another embodiment of the instant invention, a hydrogel matrix containing a controlled release element to modulate the swelling of the hydrogel for the continuous release of the potent diuretic sodium ethacrynate is prepared. Polyacrylic acid is a pH sensitive hydrogel that exhibits a greater degree of swelling at alkaline pH. To maintain the pH above 7 in the immediate environment of the polyacrylic acid, tromethamine free base crystals are coated with a microporous wall to form a controlled release element to modulate the swelling of polyacrylic acid, then mixed with the polyacrylic acid and sodium ethacrynate (drug) to form a monolithic device that releases the diuretic at a rate that is independent of environmental pH.

The C.R. tromethamine is manufactured by taking 700 g aliquots of tromethamine free base crystals passing a #20 and retained on a #30 sieve (600 micron opening) and applying a microporous wall to these crystals by standard fluidized-bed spray coating techniques. The spray solution is 100 g cellulose acetate butyrate 381-20 dissolved in a 3:1 dichloromethane/methanol solvent blend. To this, 20 g sorbitol dissolved in a water/methanol solvent blend is added as a pore forming agent influencing the release of tromethamine free base. This solution is sprayed onto the tromethamine free base crystals in a commercial Uni-Glatt fluidized-bed coating machine. The tromethamine free base crystals are coated to release tromethamine free base at a constant rate for 6-8 hours. 200 mg polyacrylic acid, 50 mg C.R. tromethamine and 50 mg sodium ethacrynate are then mixed with 15 mg polyvinylpyrrolidone 29-32K and tableted in a Manesty tableting press fitted with a ⅜" punch to yield monolithic devices which release sodium ethacrynate over several hours.

EXAMPLE 5

A matrix controlled release source of citric acid (C.R. citric) for modulation of the swelling and associated drug release from amino derivatized hydrogels is prepared as follows: citric acid, 2-hydroxyethyl methacrylate (HEMA), and ethylene glycol dimethacrylate are mixed in a 4:15:1 ratio with 8 mmoles of azobis (methylisobutyrate) added per liter of HEMA to act as a free radical polymerization initiator. The mixture is heated in a nitrogen purged vessel at 60° C. to complete polymerization to form a crosslinked, glassy mass. Upon cooling, the glassy mass is milled to a powder and sized with sieves; particles retained on a #30 sieved which pass a #20 sieve are utilized as the C.R. citric source.

Swelling modulated hydrogel matrices for the controlled release of diltiazem hydrochloride are prepared as follows: the monomers HEMA and dimethylaminoethyl methacrylate are mixed 50:50 with 8 mmoles azobis (methylisobutyrate) added per liter of monomer. To this mixture is added 10% w/w C.R. citric and 25% to 50% w/w diltiazem HCl. The composite is polymerized at 60° C. between sealed plates separated by a 1 mm thick spacer to form a sheet from which 8 mm diameter disks are cut with a cork borer. In aqueous media, the disks release diltiazem HCl at a rate which is proportional to the degree of polymer swelling. In the variable pH environment of the gastrointestinal tract the C.R. citric maintains the degree of polymer swelling, permitting a pH independent delivery of the drug.

EXAMPLE 6

Tablets for the controlled release of the drug indomethacin in accordance with the present invention are made as follows. In the formulation listed in Table 1, a core mixture of indomethacin, Aqua Keep ™ J-550 polymer and CR NaCl (see example 1) which modulates the swelling of J-550 is prepared.

TABLE 1

| TABLET Core Component | Weight |
|---|---|
| J-550 Polymer | 2 g |
| C.R. NaCl | 1 g |
| Indomethacin | 2 g |
| Avicel pH 101 | 400 mg |
| Povidone (pvp) | 60 mg in 6 ml ETOH |

A wet granulate of this mixture is mixed with ethanol/povidone until a wet slurry is formed. This slurry is then dried for a period of about 8 hours and is passed through a progression of sieves of to a final mesh size of 18. Tablet cores are prepared from the resulting granulation by taking approximately 140 mg of the granules and compressing them on a Carver® press using ¼" standard concave punches. The tablet cores prepared as above are dip coated 5 times in clear poly(vinylchloride) tablets are rolled on edge each time on a teflon sheet to prevent sticking). Each tablet is allowed to dry approximately one hour between subsequent coatings and the tablets are dried for approximately 8 hours after the fifth coat is applied.

With a small, hand-held drill three 1 mm holes are cut in each face of the coated tablets. In an aqueous environment the swelling polymer, C.R. NaCl, and drug are all expelled through the holes.

The release of indomethacin from the tablets into 1 liter of pH 7.5 phosphate buffer at 37° C. with 100 rpm stirring is then determined from U.V. absorbance readings at 320 nm.

EXAMPLE 7

The procedure of Example 5 is repeated with all conditions as described except that the device is designed as an ocular insert for placement into the conjunctival cull-de-sac of the eye and the drug is timolol at a 5% w/w loading.

What is claimed is:

1. A controlled release drug delivery device comprising a composition of:
   (a) a polymer which swells upon exposure to an aqueous environment of use;
   (b) a plurality of controlled release swelling modulators selected from the group consisting of surfactants, osmagents and buffers dispersed throughout said polymer, each of which is either coated with a microporous coating or dispersed within an individual matrix, said controlled release swelling modulators regulating the swelling of said polymer, and hence the rate of release of beneficial agent from said drug delivery device, upon exposure of said device to an aqueous environment of use;
   (c) at least one beneficial agent; and
   (d) a member comprising
      (1) a water insoluble, apertured coating surrounding said composition and wherein the aperture may vary from 10 angstroms to the size of the tablet and wherein the coating is selected from the group consisting of cellulose esters, cellulose ethers, acylated polysaccharides, polyurethanes, polyacrylates, polymethacrylates, and poly(vinylchloride) of about 1 to 1000 microns thick or
      (2) a microporous wall surrounding said composition, said microporous wall consisting of a water insoluble coating containing water soluble leachable additives of organic or inorganic origin which form pores upon exposure of said wall to an aqueous environment of use.

2. The device of claim 1, further comprising a plurality of rapid release elements selected from the group consisting of buffers osmagents and surfactants, said rapid release elements interspersed with said controlled release swelling modulators.

3. The device of claim 1, wherein said composition is laminated by adjacent microporous and semipermeable layers.

4. A controlled release drug delivery device comprising:
   (a) a first apertured layer consisting of at least one beneficial agent admixed with an excipient; and
   (b) a second layer adjacent to said first apertured layer and consisting of an admixture of a swelllable polymer, controlled release swelling modulators and rapid release elements; the polymer of said second layer swelling through said adjacent first layer upon exposure to an aqueous environment of use, thereby releasing beneficial agent from said first layer at a controlled rate; and
   (c) a member comprising (1) a water insoluble, apertured coating surrounding said layer and wherein the aperture may vary from 10 angstroms to the size of the tablet and wherein the coating is selected from the group consisting of cellulose esters, cellulose ethers, acylated polysaccharides, polyurethanes, polyacrylates, polymethacrylates, and poly(vinylchloride) of about 1 to 1000 microns thick or (2) a microporous wall surrounding said layer, said microporous wall consisting of a water insoluble coating containing water soluble leachable additives of organic or inorganic origin which form pores upon exposure of said wall to an aqueous environment of use.

5. The device of claim 1, wherein said polymer, controlled release swelling modulators and beneficial agent are admixed in a matrix substrate.

6. A method of achieving continuous or intermittant release of a beneficial agent into an aqueous environment of use comprising:

introducing a controlled release device according to claims 1 or 7 to said environment, said polymer swelling upon exposure to said aqueous environment, and thereby releasing beneficial agent, at a rate substantially determined by said controlled release swelling modulators.

* * * * *